(12) United States Patent
Antar

(10) Patent No.: US 9,351,996 B1
(45) Date of Patent: May 31, 2016

(54) TOPICAL CREAM COMPOSITION

(71) Applicant: Sayed Antar, Doral, FL (US)

(72) Inventor: Sayed Antar, Doral, FL (US)

(73) Assignee: Sayed Antar, Doral, FL (US)

( * ) Notice: Subject to any disclaimer, the term of this patent is extended or adjusted under 35 U.S.C. 154(b) by 0 days.

(21) Appl. No.: 14/644,480

(22) Filed: Mar. 11, 2015

(51) Int. Cl.
- *A61K 33/22* (2006.01)
- *A61K 8/19* (2006.01)
- *A61K 8/34* (2006.01)
- *A61K 8/362* (2006.01)
- *A61K 8/41* (2006.01)
- *A61K 8/60* (2006.01)
- *A61K 8/72* (2006.01)
- *A61K 8/81* (2006.01)
- *A61K 8/27* (2006.01)
- *A61Q 19/08* (2006.01)
- *A61K 8/63* (2006.01)

(52) U.S. Cl.
CPC . *A61K 33/22* (2013.01); *A61K 8/19* (2013.01); *A61K 8/27* (2013.01); *A61K 8/34* (2013.01); *A61K 8/345* (2013.01); *A61K 8/362* (2013.01); *A61K 8/41* (2013.01); *A61K 8/602* (2013.01); *A61K 8/63* (2013.01); *A61K 8/72* (2013.01); *A61K 8/81* (2013.01); *A61Q 19/08* (2013.01)

(58) Field of Classification Search
CPC ......... A61K 33/22; A61K 8/19; A61K 8/345; A61K 8/362; A61K 8/41; A61K 8/72; A61K 8/81; A61K 8/34; A61K 8/27; A61Q 19/08
See application file for complete search history.

(56) References Cited

U.S. PATENT DOCUMENTS

| | | | |
|---|---|---|---|
| 2007/0207107 A1* | 9/2007 | Winckle | A61K 47/24 424/70.12 |
| 2007/0218021 A1* | 9/2007 | Wells | A61K 8/062 424/59 |
| 2009/0297461 A1* | 12/2009 | Perle | A61K 8/891 424/59 |
| 2013/0315846 A1* | 11/2013 | Collier | A61K 8/97 424/59 |

FOREIGN PATENT DOCUMENTS

FR  EP 1206933 B1 * 5/2006 ............... A61K 8/34

* cited by examiner

*Primary Examiner* — Anoop Singh
*Assistant Examiner* — Doan Phan
(74) *Attorney, Agent, or Firm* — Christian Sanchelima; Jesus Sanchelima

(57) ABSTRACT

A topical skin cream composition having as one of its main objects to provide a topical skin cream having anti-biotic properties to prevent infection in wounds. In addition the combination of components in the composition help combat the effects of aging as well as help ward off psoriasis.

3 Claims, No Drawings

TOPICAL CREAM COMPOSITION

BACKGROUND OF THE INVENTION

1. Field of the Invention

The present invention relates to a topical skin cream and, more particularly, to a topical skin cream having anti-biotic, anti-wrinkle, and psoriasis treating properties.

2. Description of the Related Art

Several compositions for skin creams have been designed in the past. None of them, however, include the use of a novel combination between water, glycol, glycerin, boric acid, citric acid, tromethamine, decyl glucoside, polymethylsilsesquioxane, phenoxyethanol & Caprlyl Glycol & potassium sorbate & water & Hexylene Glycol, Stearoxymethicone/Dimethicone Copolymer, Cyclopentasiloxane & Polysilicone-11 & Ethylhexyl Hydroxystearic Acid, Talc, Glyceryl Stearate & PEG 100 Stearate, Cetyl Alcohol, Cetearyl Alcohol, Ammonium Acryloyldimethyltaurate/VP Copolymer, Stearic Acid, Cholesterol, C12-15 Alkyl Benzoate, and *Zea Mays* Oil & Cholecalciferol.

Applicant believes that a related reference corresponds to U.S. patent application No. US20090068255 issued to Yu, Betty for a use of matrix metalloproteinase inhibitors in skin care. However, it differs from the present invention because the Yu reference does not disclose the use of boric acid amongst other components required to achieve the benefits of the present invention. In addition, the Yu reference does not teach of a composition using the components of the present invention in the beneficial proportions found in the preferred embodiment of the present invention.

Other documents describing the closest subject matter provide for a number of more or less complicated features that fail to solve the problem in an efficient and economical way. None of these patents suggest the novel features of the present invention.

SUMMARY OF THE INVENTION

It is one of the main objects of the present invention to provide a topical skin cream having anti-biotic properties to prevent infection in wounds.

It is another object of this invention to provide a skin cream that also has anti-wrinkle, anti-aging and anti-scarring properties to help combat the effects of aging.

It is still another object of the present invention to provide a composition that is able to help ward off psoriasis.

It is yet another object of this invention to provide such a composition that is inexpensive to implement and maintain while retaining its effectiveness.

Further objects of the invention will be brought out in the following part of the specification, wherein detailed description is for the purpose of fully disclosing the invention without placing limitations thereon.

DETAILED DESCRIPTION OF THE EMBODIMENTS OF THE INVENTION

The present invention basically includes a composition comprising of:
a) water,
b) glycol,
c) glycerin,
d) boric acid,
e) citric acid,
d) tromethamine,
e) decyl glucoside,
f) polymethylsilsesquioxane,
g) phenoxyethanol & Caprlyl Glycol & potassium sorbate & water & Hexylene Glycol,
h) stearoxymethicone/Dimethicone Copolymer,
i) cyclopentasiloxane & Polysilicone-11 & Ethylhexyl Hydroxystearic Acid,
j) Talc,
k) Glyceryl Stearate & PEG 100 Stearate,
l) Cetyl Alcohol,
m) Cetearyl Alcohol,
n) Ammonium Acryloyldimethyltaurate/VP Copolymer,
o) Stearic Acid,
p) Cholesterol,
q) C12-15 Alkyl Benzoate,
r) *Zea Mays* Oil & Cholecalciferol,
s) Lanolin, and
t) zinc oxide & Cyclopentasiloxane & C12-15 Alkyl Benzoate & Polyhydroxystearic Acid.

In a preferred embodiment, the composition has a novel combination of the ingredients consisting of:
a) 13.6% by weight of water,
b) 3% by weight of glycol,
c) 7% by weight of glycerin,
d) 1.6% by weight of boric acid,
e) 0.1% by weight of citric acid,
d) 1.7% by weight of tromethamine,
e) 0.4% by weight of decyl glucoside,
f) 5% by weight of polymethylsilsesquioxane,
g) 0.8% by weight of phenoxyethanol & Caprlyl Glycol & potassium sorbate & water & Hexylene Glycol,
h) 10% by weight of stearoxymethicone/Dimethicone Copolymer,
i) 5% by weight of cyclopentasiloxane & Polysilicone-11 & Ethylhexyl Hydroxystearic Acid,
j) 3.6% by weight of Talc,
k) 2% by weight of Glyceryl Stearate & PEG 100 Stearate,
l) 1% by weight of Cetyl Alcohol,
m) 1.5% by weight of Cetearyl Alcohol,
n) 0.2% by weight of Ammonium Acryloyldimethyltaurate/VP Copolymer,
o) 3% be weight of Stearic Acid,
p) 1% by weight of Cholesterol,
q) 5% by weight of C12-15 Alkyl Benzoate,
r) 1% by weight of *Zea Mays* Oil & Cholecalciferol,
s) 18.5% by weight of Lanolin, and
t) 15% by weight of zinc oxide & Cyclopentasiloxane & C12-15 Alkyl Benzoate & Polyhydroxystearic Acid.

The stearic acid is an emulsifier used to stabilize the formula. The talc is used as a filler in the formula and as a diffuser of light.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A composition comprising:
a) 13.6% by weight of water,
b) 3% by weight of glycol,
c) 7% by weight of glycerin,
d) 1.6% by weight of boric acid,
e) 0.1% by weight of citric acid,
f) 1.7% by weight of tromethamine,
g) 0.4% by weight of decyl glucoside,
h) 5% by weight of polymethylsilsesquioxane, i) 0.8% by weight of phenoxyethanol & Caprlyl Glycol & potassium sorbate & water & Hexylene Glycol,
j) 10% by weight of stearoxymethicone/Dimethicone Copolymer,
k) 5% by weight of cyclopentasiloxane & Polysilicone-11 & Ethylhexyl Hydroxystearic Acid,
l) 3.6% by weight of Talc,
m) 2% by weight of Glyceryl Stearate & PEG 100 Stearate,
n) 1% by weight of Cetyl Alcohol,
o) 1.5% by weight of Cetearyl Alcohol,
p) 0.2% by weight of Ammonium Acryloyldimethyltaurate/VP Copolymer,
q) 3% be weight of Stearic Acid,
r) 1% by weight of Cholesterol,
s) 5% by weight of C12-15 Alkyl Benzoate,
t) 1% by weight of *Zea Mays* Oil & Cholecalciferol,
u) 18.5% by weight of Lanolin, and
v) 15% by weight of zinc oxide & Cyclopentasiloxane & C12-15 Alkyl Benzoate & Polyhydroxystearic Acid.

2. A composition comprising:
a) 13.6% by weight of water,
b) 3% by weight of glycol,
c) 7% by weight of glycerin,
d) 1.6% by weight of boric acid,
e) 0.1% by weight of citric acid,
f) 1.7% by weight of tromethamine,
g) 0.4% by weight of decyl glucoside,
h) 5% by weight of polymethylsilsesquioxane,
i) 0.8% by weight of phenoxyethanol & Caprlyl Glycol & potassium sorbate & water & Hexylene Glycol,
j) 10% by weight of stearoxymethicone/Dimethicone Copolymer,
k) 5% by weight of cyclopentasiloxane & Polysilicone-11 & Ethylhexyl Hydroxystearic Acid,
l) 17.6% by weight of zinc oxide & Cyclopentasiloxane & C12-15 Alkyl Benzoate & Polyhydroxystearic Acid,
m) 2% by weight of Glyceryl Stearate & PEG 100 Stearate,
n) 1% by weight of Cetyl Alcohol,
o) 1.5% by weight of Cetearyl Alcohol,
p) 0.2% by weight of Ammonium Acryloyldimethyltaurate/VP Copolymer,
q) 3% be weight of Stearic Acid,
r) 1% by weight of Cholesterol,
s) 5% by weight of C12-15 Alkyl Benzoate,
t) 1% by weight of *Zea Mays* Oil & Cholecalciferol, and
u) 19.5% by weight of Lanolin.

3. A composition comprising:
a) 14.6% by weight of water,
b) 3% by weight of glycol,
c) 7% by weight of glycerin,
d) 2.6% by weight of boric acid,
e) 0.1% by weight of citric acid,
f) 1.7% by weight of tromethamine,
g) 0.4% by weight of decyl glucoside,
h) 6% by weight of polymethylsllsesquixane,
i) 0.8% by weight of phenoxyehtanol & Caprlyl Glycol & potassium sorbate & water & Hexylene Glycol,
j) 10% by weight of stearoxymethicone/Dimethicone Copolymer,
k) 5% by weight of cyclopentasiloxane & Polysilicone-11 & Ethylhexyl Hydroxystearic Acid,
l) 17.6% by weight of zinc oxide & Cyclopentasiloxane & C12-15 Alkyl Benzoate & Polyhydroxystearic Acid,
m) 2% by weight of Glyceryl Stearate & PEG 100 Stearate,
n) 1% by weight of Cetyl Alcohol,
o) 1.5% by weight of Cetearyl Alcohol,
p) 0.2% by weight of Ammonium Acryloyldimethyltaurate/VP Copolymer,
q) 19.5% by weight of Lanolin,
r) 1% by weight of Cholesterol,
s) 5% by weight of C12-15 Alkyl Benzoate, and
t) 1% by weight of *Zea Mays* Oil & Cholecalciferol.

\* \* \* \* \*